United States Patent
Hashimoto

(10) Patent No.: US 10,206,656 B2
(45) Date of Patent: Feb. 19, 2019

(54) ULTRASONIC DIAGNOSTIC APPARATUS AND CONTROL PROGRAM THEREOF

(71) Applicant: GE Medical Systems Global Technology Company, LLC, Waukesha, WI (US)

(72) Inventor: Hiroshi Hashimoto, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 770 days.

(21) Appl. No.: 14/766,360

(22) PCT Filed: Feb. 6, 2014

(86) PCT No.: PCT/US2014/015020
§ 371 (c)(1),
(2) Date: Aug. 6, 2015

(87) PCT Pub. No.: WO2014/124088
PCT Pub. Date: Aug. 14, 2014

(65) Prior Publication Data
US 2015/0366537 A1    Dec. 24, 2015

(30) Foreign Application Priority Data

Feb. 6, 2013    (JP) ................................. 2013-021288

(51) Int. Cl.
*A61B 8/00* (2006.01)
*A61B 8/08* (2006.01)
*A61B 8/14* (2006.01)

(52) U.S. Cl.
CPC .......... *A61B 8/4416* (2013.01); *A61B 8/0841* (2013.01); *A61B 8/14* (2013.01); *A61B 8/4444* (2013.01); *A61B 8/463* (2013.01)

(58) Field of Classification Search
CPC ....... A61B 8/4416; A61B 8/0841; A61B 8/14; A61B 8/4444; A61B 8/463
See application file for complete search history.

(56) References Cited

U.S. PATENT DOCUMENTS 6,336,899 B1    1/2002  Yamazaki
2002/0173719 A1  11/2002  Zhao et al.
(Continued)

FOREIGN PATENT DOCUMENTS

CN    1636520 A    7/2005
CN    1895177 A    1/2007
(Continued)

OTHER PUBLICATIONS

International Search Report and Written Opinion issued in connection with corresponding PCT Application No. PCT/US2014/015020 dated Apr. 24, 2014.
(Continued)

*Primary Examiner* — Joel F Brutus

(57) ABSTRACT

An ultrasonic diagnostic apparatus that can identify the angle of a received ultrasonic beam with respect to the predetermined biopsy path of a biopsy needle. The ultrasonic diagnostic apparatus is characterized by including a received beam forming unit that forms received ultrasonic beams based on the echo signals of ultrasonic waves transmitted into a subject, and a display control unit that displays, in a B-mode image formed based on the received ultrasonic beams, a biopsy guide line in a display mode corresponding to an angle between the beam direction of the received ultrasonic beam and the predetermined biopsy path of a biopsy needle to be inserted into the subject. The biopsy guide line is displayed as, for example, a broken line having a width corresponding to the angle.

8 Claims, 10 Drawing Sheets

(56) References Cited

U.S. PATENT DOCUMENTS

| | | | |
|---|---|---|---|
| 2005/0090742 A1 | 4/2005 | Mine et al. | |
| 2006/0241451 A1* | 10/2006 | Nakaya | A61B 8/0833 600/443 |
| 2007/0016035 A1 | 1/2007 | Hashimoto | |
| 2008/0081993 A1 | 4/2008 | Waki | |
| 2009/0137904 A1 | 5/2009 | Wu et al. | |
| 2010/0298705 A1* | 11/2010 | Pelissier | A61B 8/0833 600/443 |
| 2012/0095339 A1 | 4/2012 | Tashiro | |

FOREIGN PATENT DOCUMENTS

| | | |
|---|---|---|
| CN | 101094611 A | 12/2007 |
| JP | 2002102221 A | 4/2002 |
| JP | 2004208859 A | 7/2004 |
| JP | 2007236767 A | 9/2007 |
| JP | 2013523343 A | 6/2013 |
| WO | 2011127191 A1 | 10/2011 |

OTHER PUBLICATIONS

Unofficial English Translation of Japanese Office Action issued in connection with corresponding JP Application No. 2013-021288 dated May 18, 2015.

Unofficial English translation of Office Action and Search Report issued in connection with corresponding on CN Application No. 201430007784.9 dated Jul. 8, 2016.

\* cited by examiner

ULTRASONIC DIAGNOSTIC APPARATUS AND CONTROL PROGRAM THEREOF

TECHNICAL FIELD

Embodiments of the present invention relate to an ultrasonic diagnostic apparatus that displays an image in a display mode corresponding to an angle between the beam direction of a received ultrasonic beam and a predetermined insertion path of a biopsy needle to be inserted into a subject, and a control program thereof.

BACKGROUND ART

An ultrasonic diagnostic apparatus can display an ultrasonic image of a subject in real time. An ultrasonic image obtained in real time allows confirmation of the position of a biopsy needle inserted into the subject.

For example, Patent Document 1 describes an ultrasonic diagnostic apparatus designed to easily distinguish a biopsy needle inserted into a subject from a body tissue. In this ultrasonic diagnostic apparatus, an ultrasonic beam is deflected substantially perpendicularly to the insertion path of the biopsy needle.

Patent Document 1: JP-A No. 2004-208859

SUMMARY OF INVENTION

The ultrasonic diagnostic apparatus described in Patent Document 1 displays a composite image of an ultrasonic image obtained based on an ultrasonic beam deflected substantially perpendicularly to an insertion path and an ultrasonic image obtained based on an ordinary ultrasonic beam. In the composite image, a part containing the ultrasonic image obtained based on the deflected ultrasonic beam clearly displays a biopsy needle, whereas the biopsy needle is less clearly displayed in a part only containing the ultrasonic image obtained by the ordinary ultrasonic beam, that is, a part not containing the ultrasonic image obtained based on the deflected ultrasonic beam as compared with the part containing the ultrasonic image obtained based on the deflected ultrasonic beam. Thus, it is difficult to recognize whether or not the biopsy needle has reached the part only containing the ultrasonic image obtained by the ordinary ultrasonic beam.

Thus, the biopsy needle in an ultrasonic image is viewed in various ways according to an angle between the beam direction of an ultrasonic beam and the biopsy needle. If an ultrasonic image contains a part clearly displaying the biopsy needle and a part unclearly displaying the biopsy needle, an operator may recognize that the biopsy needle in the unclear part has only reached the clear part. This leads to the need to identify the angle of an ultrasonic beam with respect to the biopsy needle.

If an ultrasonic beam is formed only in one direction, it is required to select a beam direction of clearly displaying the biopsy needle in an ultrasonic image before the biopsy needle is inserted.

An embodiment of the present invention provides an ultrasonic diagnostic apparatus characterized by including a received beam forming unit that forms received ultrasonic beams based on the echo signals of ultrasonic waves transmitted into a subject; and a display control unit that displays, in an ultrasonic image formed based on the received ultrasonic beams, an image in a display mode corresponding to an angle between the beam direction of the received ultrasonic beam and the predetermined biopsy path of a biopsy needle to be inserted into the subject.

According to the embodiment of the present invention, an image is displayed, in the ultrasonic image, in a display mode corresponding to an angle between the beam direction of the received ultrasonic beam and the predetermined biopsy path of the biopsy needle to be inserted into the subject. Thus, the angle of the received ultrasonic beam can be easily recognized with respect to the predetermined biopsy path of the biopsy needle with reference to the image.

DETAILED DESCRIPTION

Figure 1:
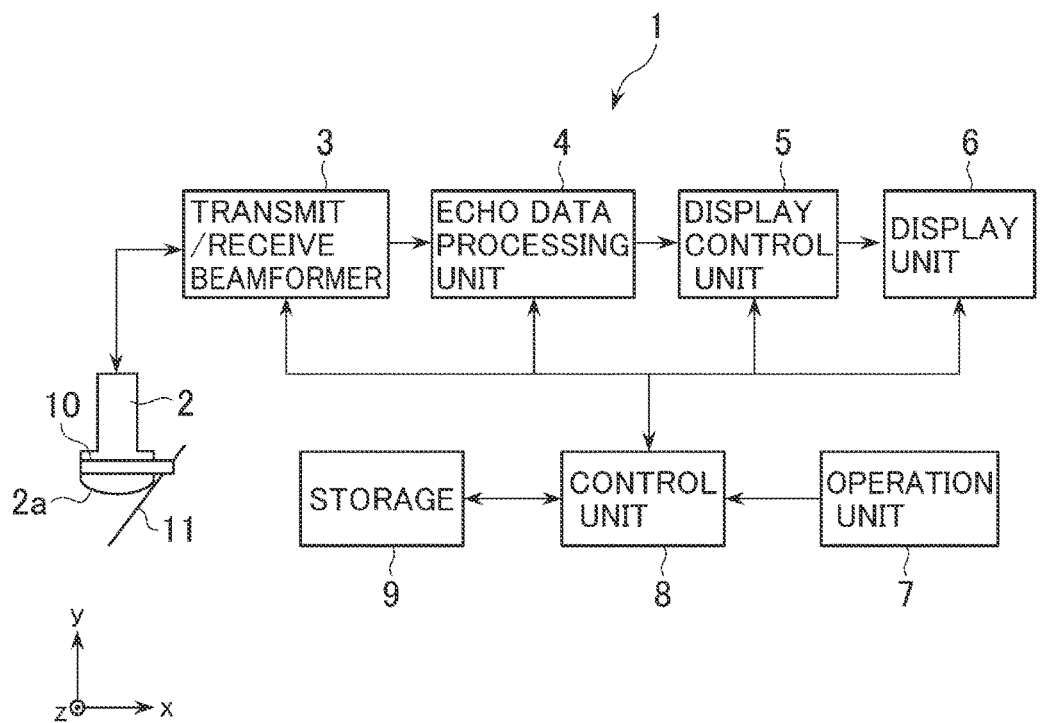
FIG. 1 is a block diagram schematically illustrating a configuration example of an embodiment of an ultrasonic diagnostic apparatus according to the present invention.

Embodiments of the present invention will be described below.

First Embodiment

Referring to FIGS. 1 to 6, a first embodiment will be first described below. An ultrasonic diagnostic apparatus 1 in FIG. 1 includes an ultrasonic probe 2, a transmit/receive beamformer 3, an echo data processing unit 4, a display control unit 5, a display unit 6, an operation unit 7, a control unit 8, and a storage 9.

The ultrasonic probe 2 includes a plurality of ultrasonic transducers disposed in an array. The ultrasonic transducer transmits an ultrasonic wave to a subject and receives the echo signal of the ultrasonic wave. In the present embodiment, the ultrasonic probe 2 is a convex ultrasonic probe 2. The ultrasonic probe 2 may be a sector ultrasonic probe.

A biopsy guide attachment 10 is detachably attached near an ultrasonic irradiation surface 2a of the ultrasonic probe 2. A biopsy needle 11 is attached to the biopsy guide attachment 10 so as to move forward and backward. The biopsy needle 11 is inserted into a guide hole (not shown) provided on the biopsy guide attachment 10, so that the biopsy needle 11 is attached to the biopsy guide attachment 10. A plurality of guide holes may be provided. The biopsy needle 11 may be inserted into the guide holes at different angles with respect to the subject.

The biopsy needle 11 attached to the biopsy guide attachment 10 is located on one end of the ultrasonic probe 2 in the azimuth direction (x axis direction in FIG. 1); meanwhile, the biopsy guide attachment 10 is mounted on the ultrasonic probe 2.

The biopsy needle 11 attached to the ultrasonic probe 2 via the biopsy guide attachment 10 can move forward and backward along the transmit/receive surface (scanning surface) of ultrasonic waves.

The transmit/receive beamformer 3 forms a transmitted/received ultrasonic beam (beam forming function). The transmitted/received ultrasonic beam is a concept including a transmitted ultrasonic beam and a received ultrasonic beam.

The transmit/receive beamformer 3 feeds a signal for transmitting a transmitted ultrasonic beam of a predetermined transmission parameter from the ultrasonic probe 2, to the ultrasonic probe 2 based on a control signal from the control unit 8.

The transmit/receive beamformer 3 performs signal processing such as A/D conversion and delayed addition and signal processing for amplification with a predetermined gain on an echo signal received by the ultrasonic probe 2, forming a received ultrasonic beam. The transmit/receive beamformer 3 is an exemplary embodiment of a received beam forming unit according to the present invention. The beam forming function is an exemplary embodiment of a received beam forming function according to the present invention.

The transmit/receive beamformer 3 outputs echo data to the echo data processing unit 4 after the signal processing.

The echo data processing unit 4 performs processing for creating ultrasonic images on the echo data outputted from the transmit/receive beamformer 3. For example, the echo data processing unit 4 generates B-mode data by performing B-mode processing including logarithmic compression and envelope demodulation.

The display control unit 5 performs a display control function. Specifically, the display control unit 5 creates B-mode image data by performing scan conversion on the B-mode data with a scan converter. The display control unit 5 displays a B-mode image on the display unit 6 based on the B-mode image data. The B-mode image is an exemplary embodiment of an ultrasonic image according to the present invention.

Figure 2:
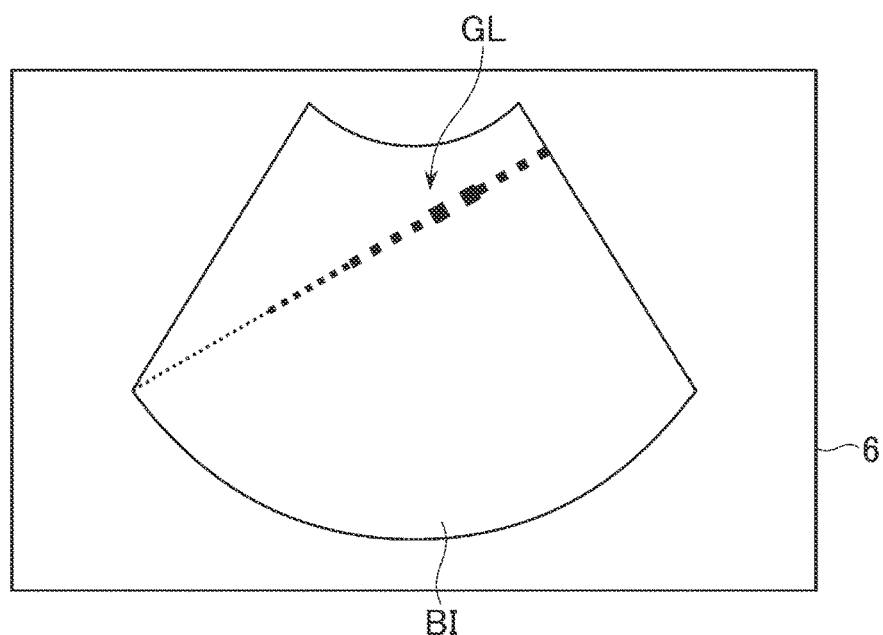
FIG. 2 is a diagram illustrating a display unit that displays a B-mode image and a biopsy guide line.

As shown in FIG. 2, the display control unit 5 displays a biopsy guide line GL, which indicates a predetermined insertion path of the biopsy needle 11, in a B-mode image BI displayed on the display unit 6. The biopsy guide line GL indicates an insertion path when the biopsy needle 11 is inserted into a subject by means of the biopsy guide attachment 10.

The storage 9 stores the position of the biopsy guide line GL in the B-mode image BI according to the type of biopsy guide attachment 10 and the position of a guide hole for inserting the biopsy needle 11 on the biopsy guide attachment 10.

The biopsy guide line GL is displayed in a display mode corresponding to an angle between the biopsy guide line GL and a transmitted/received ultrasonic beam, which will be specifically described later. The display control unit 5 is an exemplary embodiment of a display control unit according to the present invention. The biopsy guide line GL is an exemplary embodiment of an image having a display mode corresponding to an angle between the beam direction of a received ultrasonic beam and the predetermined insertion path of the biopsy needle to be inserted into a subject.

The display unit 6 is, for example, an LCD (Liquid Crystal Display) or a CRT (Cathode Ray Tube). The operation unit 7 includes a keyboard and a pointing device (not shown) that allow an operator to input instructions and information.

The control unit 8 is a CPU (CentRal Processing Unit) that reads a control program stored in the storage 9 and performs the functions of the units of the ultrasonic diagnostic apparatus 1, for example, the beam forming function and the display control function.

The storage 9 is, for example, an HDD (Hard Disk Drive) or a semiconductor memory.

The operations of the ultrasonic diagnostic apparatus 1 according to the present embodiment will be described below. The operator transmits and receives ultrasonic waves through the ultrasonic probe 2 to display the B-mode image BI on the display unit 6. The operator enters an input through the operation unit 7 to select the type of biopsy guide attachment 10 and a guide hole for inserting the biopsy needle 11. This entry specifies the biopsy guide line GL and causes the display control unit 5 to display the biopsy guide line GL on the B-mode image BI.

Figure 3:
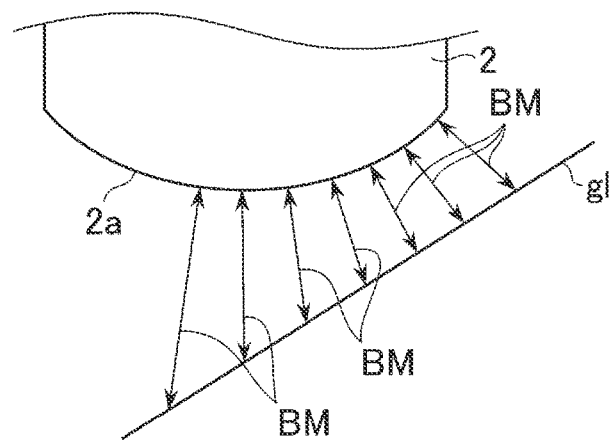
FIG. 3 is an explanatory drawing of an angle between a predetermined biopsy path and a transmitted/received ultrasonic beam.

Referring to FIG. 3, an angle between the predetermined biopsy path indicated by the biopsy guide line GL and a transmitted/received ultrasonic beam will be described below. In FIG. 3, reference character gl denotes the predetermined biopsy path and reference character BM denotes transmitted/received ultrasonic beams. The ultrasonic probe 2 sequentially transmits and receives ultrasonic waves according to sound rays, sequentially forming the transmitted/received ultrasonic beams BM. The transmitted/received ultrasonic beams BM and the predetermined biopsy path gl form different angles θ (the sign is omitted). The angles are defined as θ≤90°.

FIG. 3 illustrates only some of the transmitted/received ultrasonic beams BM.

The biopsy guide line GL is displayed in a display mode corresponding to the angle θ. The display control unit 5 determines the angle θ based on the position of the received ultrasonic beam BM in the B-mode image BI and the position of the predetermined biopsy path of the biopsy needle 11.

In the present embodiment, the biopsy guide line GL is indicated by a broken line. As illustrated in the enlarged view of FIG. 4, the biopsy guide line GL increases in width with the angle θ. The biopsy guide line GL includes a first portion P1, a second portion P2, a third portion P3, a fourth portion P4, and a fifth portion P5. The first portion P1 has the largest width, whereas the second portion P2 and the third portion P3 equally have the second largest width. Moreover, the fourth portion P4 has the third largest width while and the fifth portion P5 has the smallest width.

The angle θ is about 90° on the first portion P1. Specifically, the angle θ on the first portion P1 is expressed as 90−α≤θ≤90. For example, α is set such that the angle θ allows an operator to clearly recognize the biopsy needle 11 in the B-mode image BI (for example, α<0.5°). The angle θ on the second portion P2 and the third portion P3 is expressed as 90−β≤θ<90−α (α<β). The angle θ on the fourth portion P4 is expressed as 90−γ≤θ<90−β (β<γ). The angle θ on the fifth portion P5 is expressed as 90−δ≤θ<90−γ (γ<δ).

If the angle θ is about 90°, the biopsy needle 11 is clearly displayed in the B-mode image BI. As the angle θ decreases from 90°, the biopsy needle 11 becomes more unclear in the B-mode image BI. Referring to the width of the biopsy guide line GL, the angle of the transmitted/received ultrasonic beam BM can be easily identified relative to the predetermined biopsy path gl of the biopsy needle 11. A fine pattern on the biopsy guide line GL allows an operator to observe the B-mode image BI in consideration of the unclearly displayed biopsy needle 11 in the B-mode image BI. The biopsy needle 11 can be observed in consideration of how the biopsy needle 11 is displayed according to the angle θ, allowing the operator to easily confirm whether the biopsy needle 11 has reached a point or not.

Figure 4:
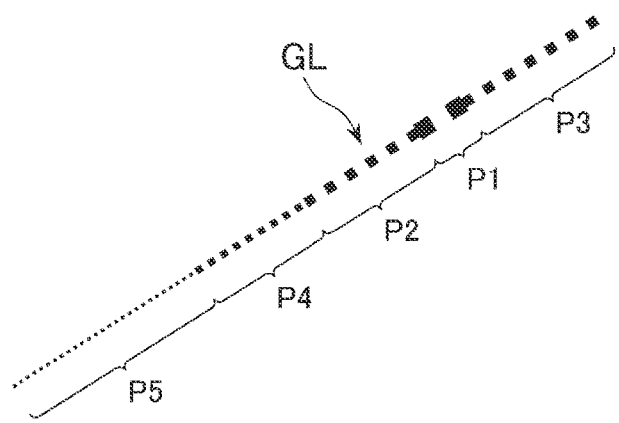
FIG. 4 is an enlarged view of the biopsy guide line.
Figure 5:
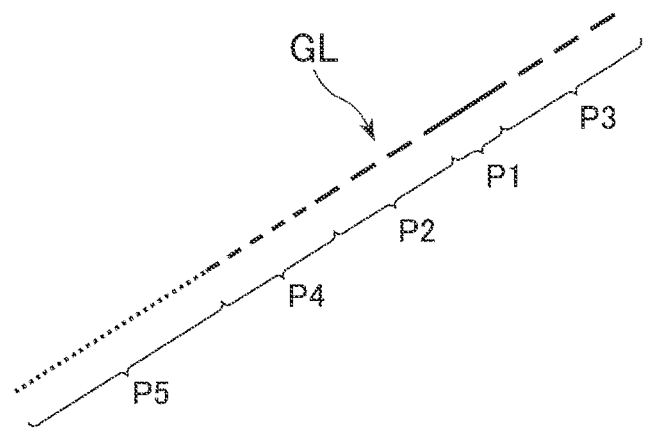
FIG. 5 is an enlarged view of another example of the biopsy guide line.

In the first embodiment, the display modes of the biopsy guide line GL are not limited to those of FIG. 4 as long as the biopsy guide line GL partially varies in display mode according to the angle θ. For example, as shown in FIG. 5, the biopsy guide line GL may be represented as a solid line and kinds of broken lines. In FIG. 5, the first portion P1 is expressed as a solid line, whereas the second portion P2, the third portion P3, the fourth portion P4, and the fifth portion P5 are expressed as different types of broken lines that depend upon the angle θ.

Figure 6:
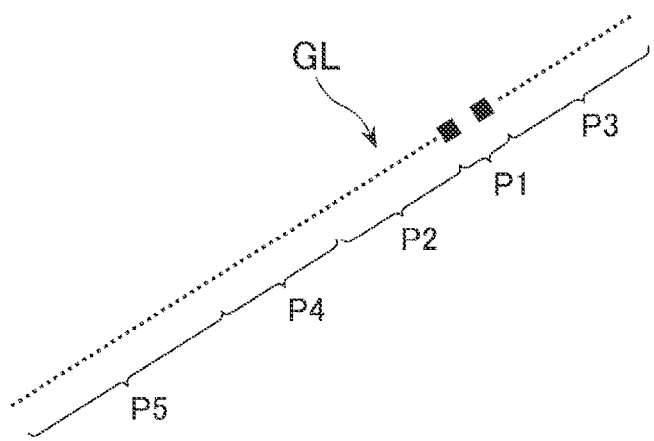
FIG. 6 is an enlarged view of still another example of the biopsy guide line.

As shown in FIG. 6, the first portion and other portions (the second portion P2 to the fifth portion P5) of the biopsy guide line GL may be displayed in different display modes. In FIG. 6, the first portion P1 is different in width from the second portion P2 to the fifth portion P5. Since the first portion P1 and other portions of the biopsy guide line GL are displayed in different display modes, a portion where the angle θ is about 90° can be distinguished from other portions. Thus, an operator can observe the B-mode image BI in consideration of a part containing the unclearly displayed biopsy needle 11 in the B-mode image BI.

In the explanation, the biopsy guide line GL is displayed in different display modes in the four ranges of 90−α≤θ≤90, 90−β≤θ<90−α, 90−γ≤θ<90−β, and 90−δ≤θ<90−γ. The angle θ in different display modes is not limited to these ranges. For example, the biopsy guide line GL may be displayed in different display modes for the respective degrees of the angle θ.

Second Embodiment

A second embodiment will be described below. Only different matters from the first embodiment will be discussed below.

An ultrasonic diagnostic apparatus 1 of the present embodiment is identical in configuration to that of the first embodiment. The ultrasonic probe 2 of the present embodiment is a linear ultrasonic probe.

Figure 7:
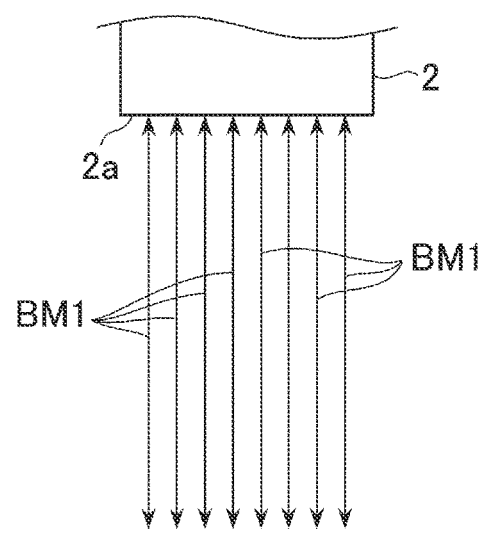
FIG. 7 is a diagram illustrating the beam direction of transmitted/received ultrasonic beams according to a second embodiment.
Figure 8:
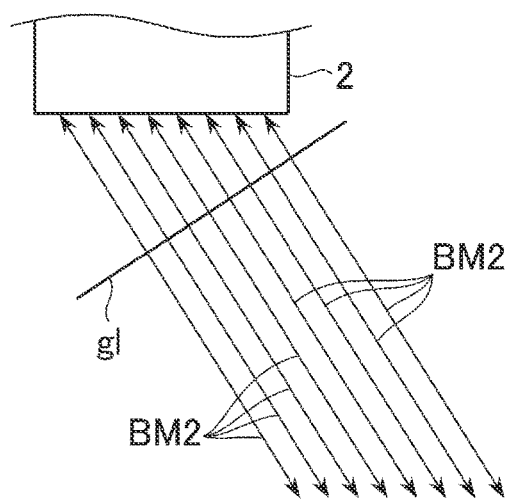
FIG. 8 is a diagram illustrating the beam direction of other transmitted/received ultrasonic beams according to the second embodiment.
Figure 9:
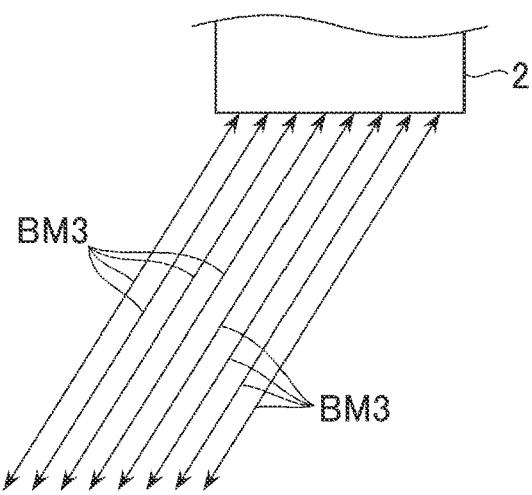
FIG. 9 is a diagram illustrating the beam direction of other transmitted/received ultrasonic beams according to the second embodiment.

In the present embodiment, transmitted/received ultrasonic beams in multiple directions are formed and then a composite ultrasonic image is obtained based on the transmitted/received ultrasonic beams. In the present embodiment, as shown in FIGS. 7 to 9, transmitted/received ultrasonic beams BM1 to BM3 are formed in three directions. Specifically, the transmitted/received ultrasonic beams BM1 in FIG. 7 are perpendicular to an irradiation surface 2a of the ultrasonic probe 2. The transmitted/received ultrasonic beams BM2 in FIG. 8 and the transmitted/received ultrasonic beams BM3 in FIG. 9 are tilted by an equal angle in different directions with respect to the transmitted/received ultrasonic beams BM1. An angle θ between the transmitted/received ultrasonic beams BM2 and the predetermined biopsy path gl of the biopsy needle 11 is about 90°, whereas an angle θ between the transmitted/received ultrasonic beams BM1 and BM3 and the predetermined biopsy path gl is smaller than 90°.

Figure 10:
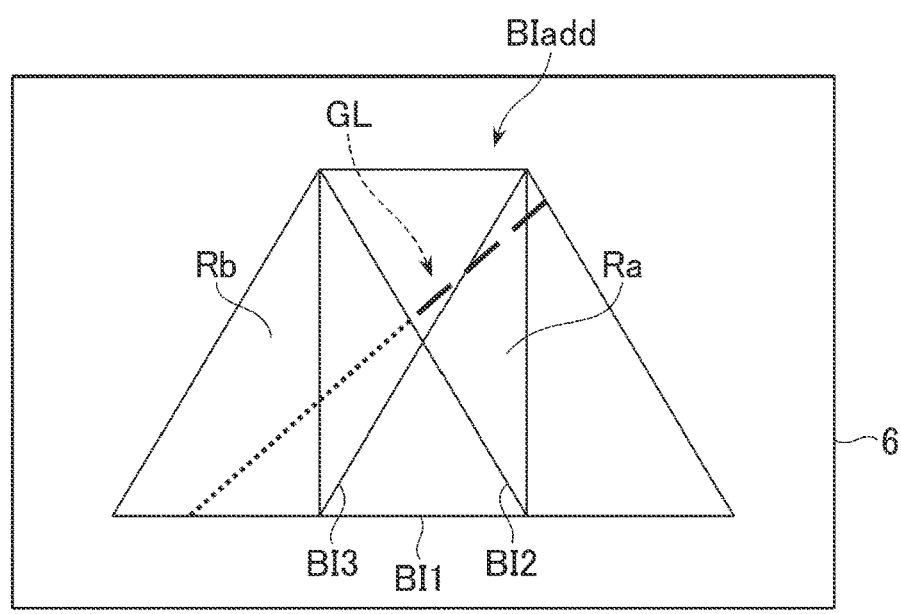
FIG. 10 is a diagram of a display unit that displays a composite image.

For example, the ultrasonic probe 2 transmits and receives ultrasonic waves for forming the transmitted/received ultrasonic beams BM1 and then transmits and receives ultrasonic waves for forming the transmitted/received ultrasonic beams BM2. After that, the ultrasonic probe 2 transmits and receives ultrasonic waves for forming the transmitted/received ultrasonic beams BM3. The display control unit 5 adds up a B-mode image BI1 based on the transmitted/received ultrasonic beams BM1, a B-mode image BI2 based on the transmitted/received ultrasonic beams BM2, and a B-mode image BI3 based on the transmitted/received ultrasonic beams BM3 to obtain a composite image BIadd that is displayed on the display unit 6 as shown in FIG. 10. In FIG. 10, the edges of the B-mode images BI1 to BI3 are illustrated for the sake of explanation but are not displayed in the actual composite image BIadd.

As shown in FIG. 10, the display control unit 5 displays a biopsy guide line GL in the composite image BIadd displayed on the display unit 6. Also in the present embodiment, an operator's input through the operation unit 7 displays the biopsy guide line GL.

Also in the present embodiment, the biopsy guide line GL is displayed in a display mode corresponding to an angle θ between a transmitted/received ultrasonic beam BM and the predetermined biopsy path gl (biopsy guide line GL). In the present embodiment, the biopsy guide line GL is expressed as different broken lines in an area Ra containing the formed transmitted/received ultrasonic beams BM2 and an area Rb other than the area Ra.

The area Ra containing the transmitted/received ultrasonic beams BM2 includes a composite area of a part of the B-mode image BI2 and a part of the B-mode image BI1 and an area only including the B-mode image BI2 (parallelogram area). In the area Ra, the angle θ between the transmitted/received ultrasonic beam BM2 and the biopsy guide line GL is about 90°, which clearly displays the biopsy needle 11 in the composite image BIadd.

The area Rb other than the area containing the formed transmitted/received ultrasonic beams BM2, that is, an area only containing the transmitted/received ultrasonic beams BM1, an area containing the transmitted/received ultrasonic beams BM1 and BM3, and an area containing the ultrasonic beams BM3 are an area only containing the B-mode image BI1, a composite area of the B-mode image BI1 and the B-mode image BI3, and an area containing only the B-mode image BI3 (triangular area).

For a part containing the transmitted/received ultrasonic beams BM, for example, a larger angle is used as the angle θ. In the area Ra including a part containing the transmitted/received ultrasonic beams BM1, for example, an angle between the transmitted/received ultrasonic beam BM2 and the predetermined biopsy path gl is larger than an angle between the transmitted/received ultrasonic beam BM1 and the predetermined biopsy path gl. Thus, the display mode of the biopsy guide line GL in the area Ra is determined by the angle θ that is an angle between the transmitted/received ultrasonic beam BM2 and the predetermined biopsy path gl.

According to the present embodiment, the biopsy guide line GL in the area with the angle θ of about 90° is displayed in a different display mode from the other area. Thus, as in the first embodiment, a B-mode image BI can be observed in consideration of a part where the biopsy needle 11 is unclearly displayed in the B-mode image BI.

Figure 11:
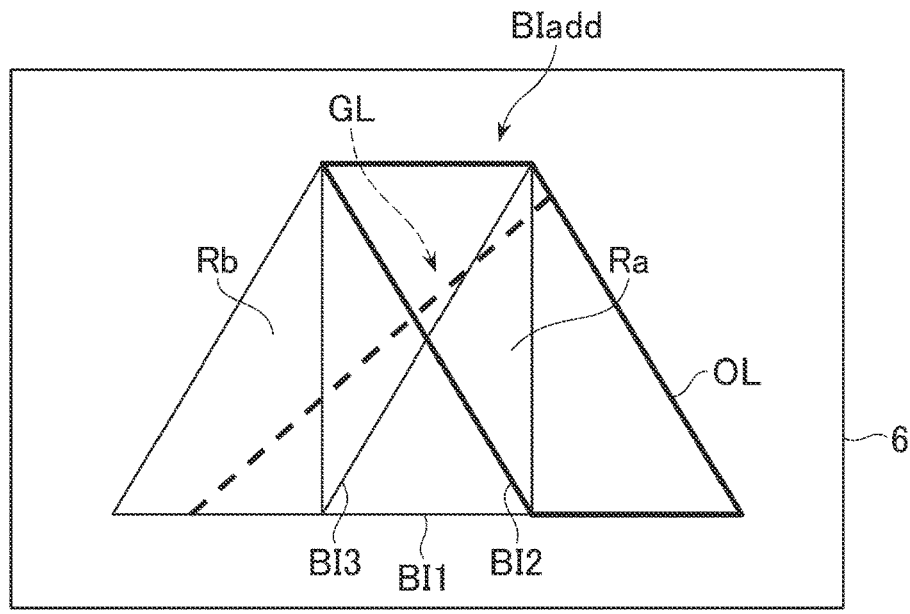
FIG. 11 is a diagram of a display unit according to a first modification of the second embodiment.

Modifications of the second embodiment will be described below. A first modification will be first discussed below. In the first modification, as shown in FIG. 11, the display control unit 5 displays an edge OL, which defines the area Ra containing the received ultrasonic beams BM2, on the display unit 6. The edge OL is an exemplary embodiment of an area defining image that indicates the area of received ultrasonic beams formed in the same direction.

Also in the first modification, the area containing the transmitted/received ultrasonic beams BM perpendicular to the predetermined biopsy path gl of the biopsy needle 11 in the B-mode image BI can be distinguished from the other area by the edge OL. This allows an operator to observe the B-mode image BI in consideration of a part where the biopsy needle 11 is clearly displayed and a part where the biopsy needle 11 is unclearly displayed.

In the first modification, the edge OL may be displayed on the area Rb instead of the area Ra. The edge OL on the area Rb is not particularly illustrated. The edge OL displayed on the area Rb allows an operator to distinguish an area containing the transmitted/received ultrasonic beams BM perpendicular to the predetermined biopsy path gl of the biopsy needle 11 from the other area.

Figure 12:
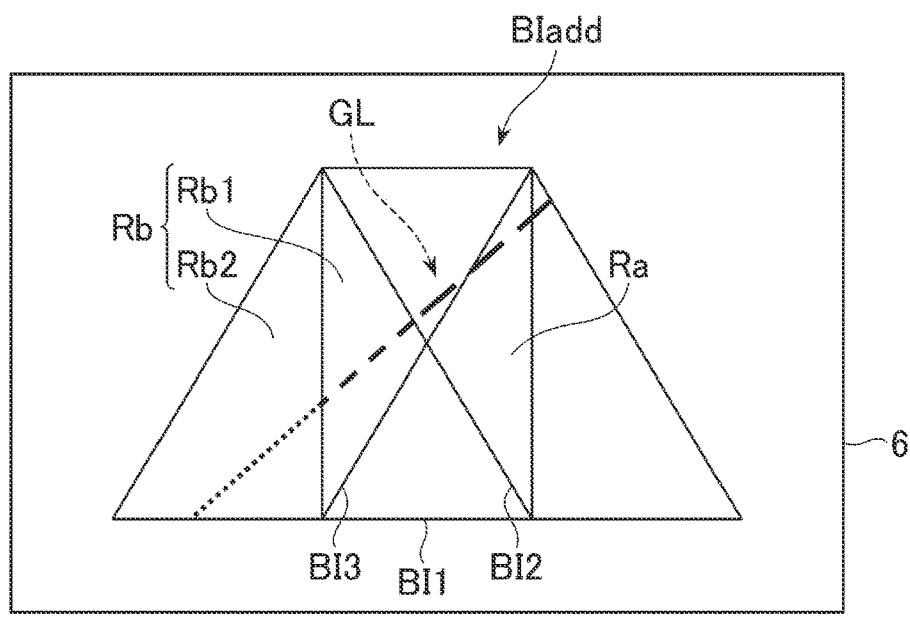
FIG. 12 is a diagram of a display unit according to a second modification of the second embodiment.

A second modification will be described below. In this modification, as shown in FIG. 12, the biopsy guide line GL in the area Ra containing the transmitted/received ultrasonic beams BM2 is displayed in a different display mode from the other area Rb. In the area Rb, the biopsy guide line GL in an area Rb1 is displayed in a different display mode from an area Rb2. In FIG. 12, the biopsy guide line GL is indicated by different kinds of broken lines in the area Ra, the area Rb1, and the area Rb2.

The area Rb1 in the area Rb contains the transmitted/received ultrasonic beams BM1. The area Rb1 includes an area containing only the B-mode image BI1 and a composite area of the B-mode image BI1 and the B-mode image BI3. The area Rb2 in the area Rb only contains the transmitted/received ultrasonic beams BM3. The area Rb2 only includes the B-mode image BI3.

In this modification, the biopsy guide line GL is indicated by three kinds of broken lines and partially varies in display mode according to the angle θ. This allows an operator to observe the biopsy needle 11 in consideration of how the biopsy needle 11 is displayed according to the angle θ.

Figure 13:
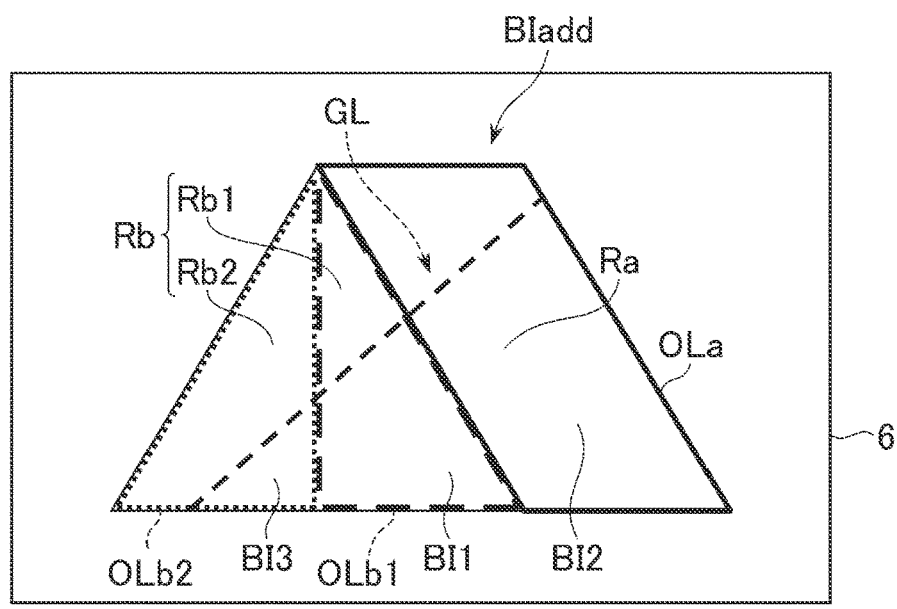
FIG. 13 is a diagram of a display unit according to a third modification of the second embodiment.

A third modification will be described below. In this modification, as shown in FIG. 13, an edge OLa on the area Ra, an edge OLb1 on the area Rb1, and an edge OLb2 on the area Rb2 are displayed. The edges OLa, OLb1, and OLb2 are displayed in different display modes. The edge OLa is indicated by a solid line in FIG. 13. The edges OLb1 and OLb2 are different kinds of broken lines.

The edges of the B-mode image BI1 and the B-mode image BI3 are shown in the other drawings for the sake of explanation but are not shown in FIG. 13.

In this modification, the edges OLa, OLb1, and OLb2 are displayed in different display modes according to the angle θ, allowing an operator to observe the biopsy needle 11 in consideration of how the biopsy needle 11 is displayed according to the angle θ.

Third Embodiment

A third embodiment will be described below. Only different matters from the first and second embodiments will be discussed below.

Also in the present embodiment, as in the second embodiment, ultrasonic waves are transmitted and received by a linear ultrasonic probe to form the transmitted/received ultrasonic beams BM1 to BM3. Unlike in the second embodiment, a composite image BIadd of the B-mode images BI1 to BI3 is not created. In the present embodiment, transmission and reception are switched among ultrasonic waves for forming the transmitted/received ultrasonic beams BM1, ultrasonic waves for forming the transmitted/received ultrasonic beams BM2, and ultrasonic waves for forming the transmitted/received ultrasonic beams BM3. Thus, a B-mode image BI is displayed based on one of the transmitted/received ultrasonic beams BM1 to BM3. The transmitted/received ultrasonic beams BM1 to BM3 are switched based on an operator's input on the operation unit 7.

Figure 14:
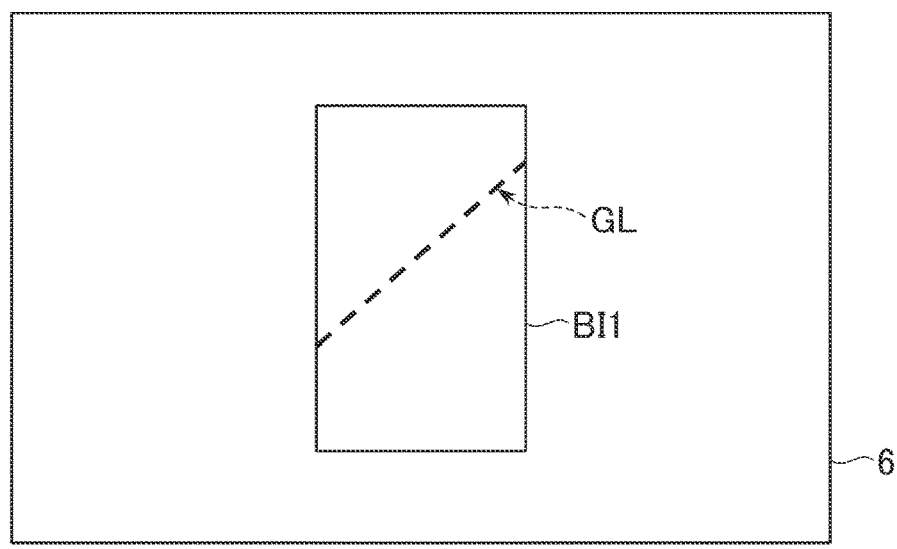
FIG. 14 is a diagram of a display unit that displays a B-mode image according to a third embodiment.
Figure 15:
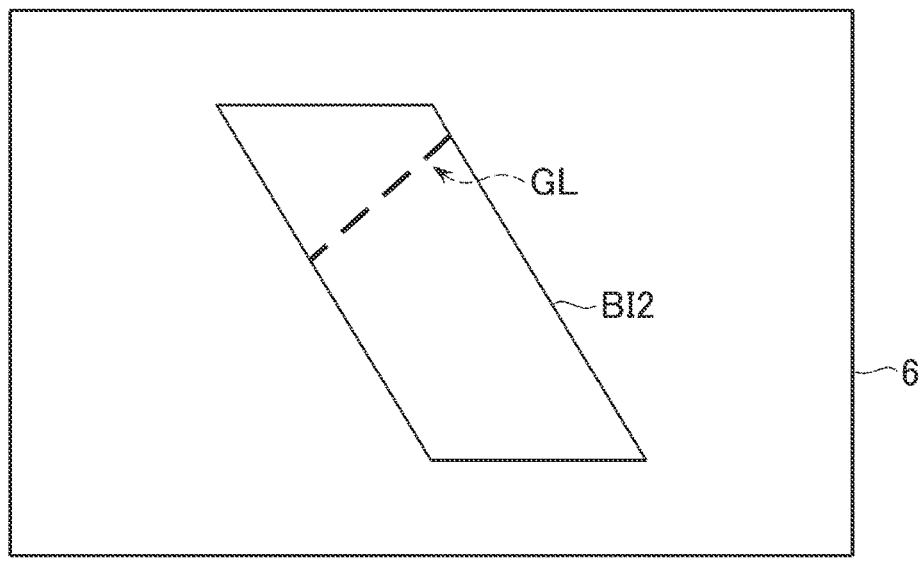
FIG. 15 is a diagram of a display unit that displays another B-mode image according to the third embodiment.
Figure 16:
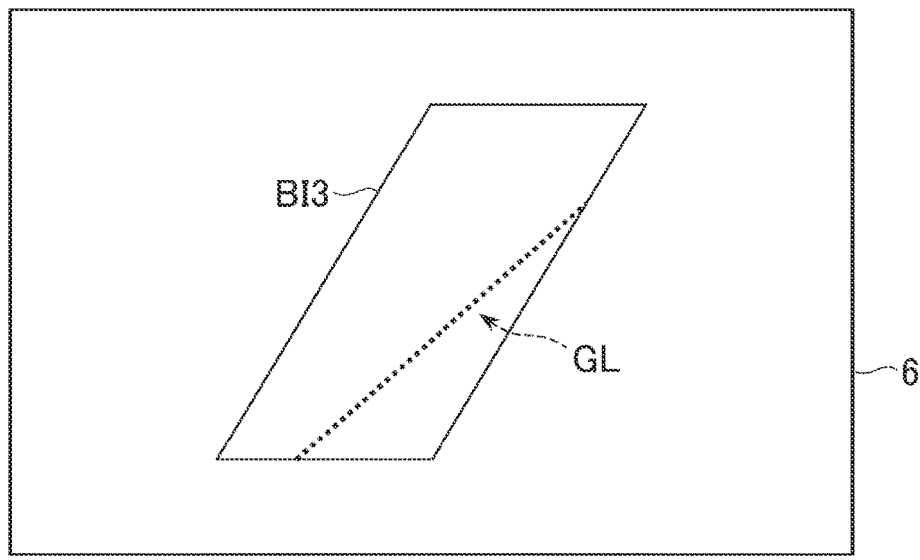
FIG. 16 is a diagram of a display unit that displays still another B-mode image according to the third embodiment.

As shown in FIGS. 14 to 16, a biopsy guide line GL is displayed in a display mode corresponding to the angle θ in the B-mode images BI1 to BI3. In the present embodiment, the biopsy guide line GL is indicated by different kinds of broken lines according to the angle θ.

According to the present embodiment, an operator switches the beam directions of the transmitted/received ultrasonic beams BM to display one of the B-mode images BI1 to BI3 before inserting a biopsy needle 11. The biopsy guide line GL is displayed in a display mode corresponding to the angle θ in the B-mode images BI1 to BI3, allowing the operator to easily recognize a beam direction of most clearly displaying the biopsy needle 11. Thus, before the insertion of the biopsy needle 11, the operator can easily select the beam direction of most clearly displaying the biopsy needle 11.

In the present embodiment, the beam direction of the transmitted/received ultrasonic beam BM2 allows the biopsy needle 11 to be most clearly displayed. Thus, the operator selects the beam direction of the transmitted/received ultrasonic beam BM2 to display the B-mode image BI2, and then inserts the biopsy needle 11.

Figure 17:
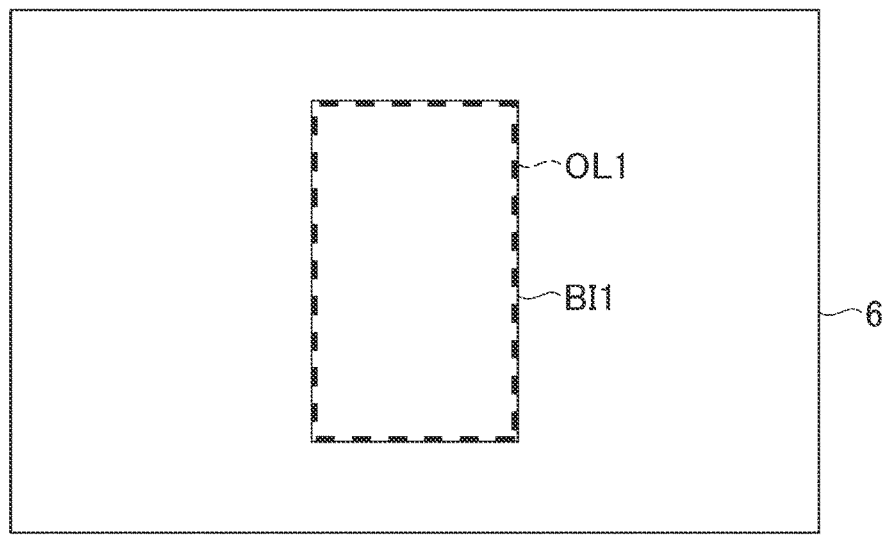
FIG. 17 is a diagram of a display unit that displays a B-mode image according to a modification of the third embodiment.
Figure 18:
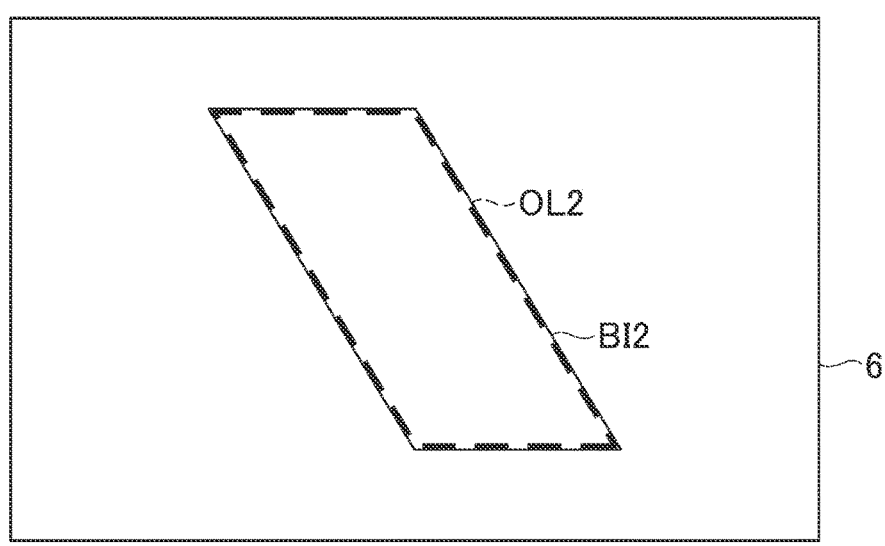
FIG. 18 is a diagram of a display unit that displays still another B-mode image according to the third embodiment.
Figure 19:
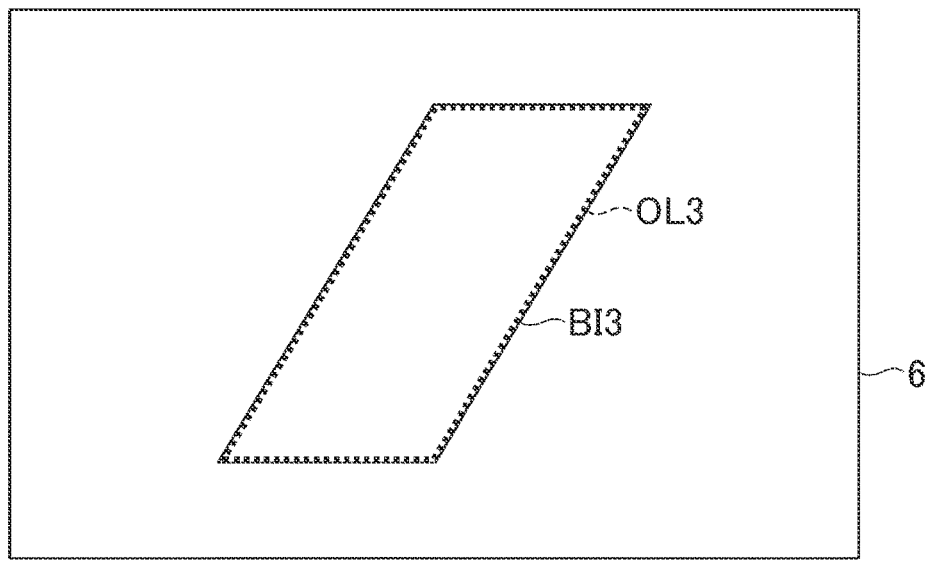
FIG. 19 is a diagram of a display unit that displays still another B-mode image according to the third embodiment.

A modification of the third embodiment will be described below. In this modification, as shown in FIGS. 17 to 19, the B-mode images BI1 to BI3 have edges OL1, OL2, and OL3 that are displayed in display modes according to the angle θ. In this modification, the edges OL1, OL2, and OL3 are different kinds of broken lines.

The present invention was described with reference to the foregoing embodiments. As a matter of course, the present invention can be changed within the scope of the present invention. For example, the display modes of the biopsy guide line GL are not limited to those of the foregoing embodiments and may vary in color according to the angle θ. The edge OL may also vary in color according to the angle θ.

The images of the area Ra and the areas Rb, Rb1, and Rb2 are not limited to the edges OL, OLa, OLb1, and OLb2. For example, the area Ra and the areas Rb, Rb1, and Rb2 may be colored. In this case, the areas vary in color according to the angle θ. If the areas are colored, the areas are made transparent to the B-mode image BI on the background.

For example, if the focus of a transmitted ultrasonic beam is not formed, the angle θ is formed between the beam direction of a received ultrasonic beam and the predetermined biopsy path gl.

What is claimed is:

1. An ultrasonic diagnostic apparatus, comprising:
   a received beam forming unit that forms a plurality of received ultrasonic beams based on echo signals of ultrasonic waves transmitted into a subject, wherein the plurality of received ultrasonic beams includes a first subset of the plurality of received ultrasonic beams that intersects a predetermined biopsy path of a biopsy needle within a first range of angles and a second subset of the plurality of received ultrasonic beams that intersects the predetermined biopsy path of the biopsy needle within a second range of angles that is different than the first range of angles; and
   a display control unit that displays, in an ultrasonic image formed based on the received ultrasonic beams, a biopsy guide line indicating the predetermined biopsy path of the needle, the biopsy guide line being displayed in multiple different display modes at the same time, including a first display mode corresponding to the first subset of the plurality of received ultrasonic beams that interests the predetermined biopsy path within the first range of angles and a second display mode corresponding to the second subset of the plurality of received ultrasonic beams that intersects the predetermined biopsy path within the second range of angles.

2. The ultrasonic diagnostic apparatus of claim 1, wherein the first display mode is a solid line and the second display mode is a broken line.

3. The ultrasonic diagnostic apparatus of claim 1, wherein the first display mode is a first type of broken line and the second display mode is a second type of broken line.

4. The ultrasonic diagnostic apparatus of claim 1, wherein a width of the biopsy guideline in the first display mode is different than a width of the biopsy guideline in the second display mode.

5. A method of controlling an ultrasonic diagnostic apparatus, the method comprising:
   forming a plurality of received ultrasonic beams based on echo signals of ultrasonic waves transmitted into a subject, wherein the plurality of received ultrasonic beams includes a first subset of the plurality of received ultrasonic beams that intersects a predetermined biopsy path of a biopsy needle within a first range of angles and a second subset of the plurality of received ultrasonic beams that interests the predetermined biopsy path of the biopsy needle within a second range of angles that is different than the first range of angles; and
   displaying, in an ultrasonic image formed based on the received ultrasonic beams, a biopsy guide line indicating the predetermined biopsy path of the biopsy needle, the biopsy guide line being displayed in multiple different display modes at the same time, including a first display mode corresponding to the first subset of the plurality of received ultrasonic beams that interests the predetermined biopsy path within the first range of angles and a second display mode corresponding to the second subset of the plurality of received ultrasonic beams that intersects the predetermined biopsy path within the second range of angles.

6. The method of claim 5, wherein the first display mode is a solid line and the second display mode is a broken line.

7. The method of claim 5, wherein the first display mode is a first type of broken line and the second display mode is a second type of broken line.

8. The method of claim 5, wherein a width of the biopsy guideline in the first display mode is different than a width of the biopsy guideline in the second display mode.

* * * * *